United States Patent
Gaber

(12) 
(10) Patent No.: US 6,296,618 B1
(45) Date of Patent: Oct. 2, 2001

(54) PRE/POST- COMPRESSION REHABILITATION GARMENT

(76) Inventor: Faith Gaber, 1102 Epworth Ct., Baltimore, MD (US) 21234

(*) Notice: Subject to any disclaimer, the term of this patent is extended or adjusted under 35 U.S.C. 154(b) by 0 days.

(21) Appl. No.: 09/455,765

(22) Filed: Dec. 7, 1999

(51) Int. Cl.⁷ .............................. A61F 13/00; A61F 5/00
(52) U.S. Cl. .............................. 602/75; 602/19; 602/60; 602/61; 24/442
(58) Field of Search .......................... 24/442–452, 306; 2/912–919, 114, 51, 83, 920, 311, 312, 321, 322; 604/391; 602/74, 75; 128/DIG. 15

(56) References Cited

U.S. PATENT DOCUMENTS

| | | |
|---|---|---|
| Re. 34,662 | 7/1994 | Keller . |
| 1,466,598 | 8/1923 | Panes . |
| 3,968,803 | 7/1976 | Hyman . |
| 4,665,909 * | 5/1987 | Trainor ................................... 602/75 |
| 4,937,887 * | 7/1990 | Schreiner ................................ 2/402 |
| 5,084,914 | 2/1992 | Hesch . |
| 5,133,112 * | 7/1992 | Gomez-Acevedo ................... 24/450 |
| 5,146,932 * | 9/1992 | McCabe ............................... 128/873 |
| 5,315,716 | 5/1994 | Baum . |
| 5,410,758 * | 5/1995 | Dupont et al. ............................ 2/51 |
| 5,527,270 * | 6/1996 | Chase ..................................... 602/41 |
| 5,535,449 * | 7/1996 | Dickey ..................................... 2/69 |
| 5,693,401 * | 12/1997 | Sommers et al. ..................... 428/100 |
| 6,080,347 * | 6/2000 | Goulait ................................. 264/167 |

* cited by examiner

Primary Examiner—Kim M. Lewis
(74) Attorney, Agent, or Firm—Hoffman Wasson & Gitler

(57) ABSTRACT

A pre or post-operative surgical compression garment composed of Lycra and cotton including one or more strips of flexible fabric fastener, also used for triage. The flexible fabric fastener comprises a flexible and stretchable polyester and rubber elastic material in which Velcro®-type nylon loops on the male part or hooks on the female part are woven there through. The Velcro®-type hooks or loops will cover alternative portions of the elastic base composing the elements of the flexible fabric fastener. One strip of the flexible fabric fastener is sewn with polyester and rubber thread to the underside of the top flap of the garment. Two evenly spaced parallel strips are sewn on the top of the second flap affording the opportunity for horizontal multi-sizing in one garment and vertical stretch. Each compression garment is supplied with multi-support panels for chest, back, abdomen, and inner and outer leg portions for comfort. Thin elastic waistband, the cotton stretchable cuffs, seamless construction, multi-sizing at all closures reduces binding, riding up of materials on the body parts. Garments are designed for speed and ease of application by healthcare workers during triage or after surgery and patient, physical comfort visibly pleasing in its colors and patterns. These garments include a replaceable cradle for protecting the crotch area. These body bandage garments are age appropriate and non-gender specific.

17 Claims, 8 Drawing Sheets

PRE/POST- COMPRESSION REHABILITATION GARMENT

FIELD OF THE INVENTION

The present invention is directed to a pre or post-surgical compression garment provided with a flexible fabric fastener allowing healthcare providers or a patient to easily don and remove the garment.

BACKGROUND OF THE INVENTION

Various surgical procedures such as liposuction, reconstructive surgery, cancer surgery or emergency triage events would tend to produce pre or post-operative heavy bleeding or swelling in one or more areas of the patient. When this occurs, the patient would find it difficult to utilize his or her bed garments, such as pajamas or nightgowns or other street clothes immediately after a surgical procedure or at an accident event. The patient would have one or more areas of swelling or bleeding preventing the patient's own garment from holding medically placed absorbent pads in the correct location and being sanitary. Additionally, these garments might also irritate, contaminate or infect any sutures used to close incisions or wounds of the patient after the surgery or accident. Further, conventional bed garments or street clothes are not produced of a material that is capable of compressing the skin to subcutaneous body parts. Additionally, the patient's conventional bed garments would make it difficult to open and close the garment for various reasons, such as the evacuation of bodily functions or changing the dressings and absorbent pads required after surgery.

A number of garments have been produced which try to address this particular problem. For example, U.S. Pat. No. 5,315,716, issued to Baum is directed to pants for recreational use and for physically infirmed or handicapped persons allowing the pants to be easily donned and removed. A releasable seam along the outside of each leg of these pants provided with separate hook and loop fastener segments would assist in allowing handicapped or infirmed persons to open and close the pants. Unfortunately, these side openings would cause the patient to twist and bend the body in order to open and close these releasable seams. The Baum closure places hooks and eyes below the Velcro® fastener corresponding to areas in which surgical sutures would be placed, thereby causing pain to the patient and difficulty applying and removing the garment.

Similarly, U.S. Pat. No. 5,084,914, issued to Hesch illustrates an invalid garment having opening and closing slits placed in the back of the trouser leg. This slits are opened and closed utilizing Velcro® fasteners. The position of this opening would make it difficult for the patient to easily remove the garment without assistance from other individuals. A stiff Velcro® fastener utilized by Hesch would also make it difficult for a patient or healthcare provider to apply and remove the garment as well as potentially cause pain when the patient physically moves. Furthermore, once the patient's swelling or bleeding begins to decrease, the garments described in the Baum and Hesch patents would cause the garment to become ill-fitting. This would result in the patient having to purchase a second, smaller garment.

U.S. Pat. No. 3,968,803, issued to Hyman describes a surgical chest dressing provided with two non-elastic and non-stretchable strips 30, 32 used as Velcro® fastening elements. However, as is true with respect to the Hesch invalid garment, the non-elastic nature of the strips would make it difficult for the patient to easily move in or size the garment, particularly immediately after surgery.

The E-Z-ON Medical Surgical Supply Company produces a number of compression garments. These garments, while including two side openings, utilize thick stiff zippers that force the patient to twist and turn to open and close the garment. The ends of the zippers include a sharp nylon construction scratching the skin of the patient. The patient needs to bend from the waist to the knee in order to fit the zipper parts together after bending and hooking hooks in order to reapply the garment. This operation must be done for both sides of the garment and is quite painful to swollen limbs. When the zipper is re-applied, it becomes stiff and thick and difficult to bend the body against it, thereby causing unnecessary pain to the healing sites. Sets of market produced hook-and-eyes are sewn onto the garment underneath the zipper. Hooks-and-eyes press against the skin at the surgical incision sites causing the patient undue pressure and pain. Additionally, the thickness of these pieces cause difficulty for a patient to roll over in bed, each of these garments would incorporate only a single size, thereby requiring the patient to purchase additional, smaller garments as the swelling subsides.

More specifically, the E-Z-ON garments have no woven in or sewn in support panels for the breast/chest area or the back. For the lower body garment, there are no support panels or very limited support panels. A half square pattern sewn over the garment hides a bulky seam that impinges on the body of the patient. The male version of this garment does not have this panel.

The E-Z-ON upper body garment for male and female have under arm side seams that are extra bulky against the skin. The lower body garments for the females have inner thigh seams and outer waist to below the knee seams causing impingement on the body. Having four parts of a garment to cut and sew is a timely and costly method of production. Several of the E-Z-ON garments have upper body convenient frontal openings and Velcro® closures at the shoulders. E-Z-ON has several lower body garments having two side openings with thick stiff zippers that force the patient to twist and turn to open or close these garments. The ends of the zipper have unfinished ends leaving the sharp nylon construction to scratch the skin of the patient. The patient needs to bend from the waist to the knee in order to fit the zipper parts together after bending and hooking the hooks first, in order to reapply the garment. The patient may need to do this for both sides. This activity is quite painful on swollen limbs. When the zipper is reapplied it becomes stiff and thick to bend the body against it to do the other side, causing unnecessary pain to the healing sites. Market produced hooks and eyes are sewn onto the garment underneath the zipper. The hooks and eyes press against the skin or at the surgical incision sites causing the patient undue pressure and pain. For the male garments zippers, hook and eye closures that are found at the inner thigh going from crotch to leg cause the patient to bend all the way over to this area, sit and try to manipulate the closure or get someone else to assist in the procedure.

Prior art does not illustrate a flexible fabric fastener. Zippers and hooks and eyes as closures are bulky due to layers of these devices and placket fabric coverings. For patients using garments with zippers on either side of the inner leg causes difficulty in walking and can chafe the skin. The garments with the zippers on the outer sides of the garment are stiff and bending at knees and hips remain difficult to maneuver stairs, laying down or getting out of bed. It is more difficult to roll over in bed against the thick edge of the inserted devices.

Additionally, the prior art does not employ any multiple sizing used in a single garment.

The E-Z-ON garments are provided with a three inch waist band on the lower body garment. It generates a binding feeling for the wearer. When the wearer bends over to manipulate closing the garment or putting on outer wear, the wide waste band bends in half doubling it's thickness at the waist. It cuts into the skin leaving a red mark. It becomes more difficult to have flexible body movement and is uncomfortable to sit in.

The E-Z-ON garments are not equipped with a folded hem. The zipper leaves the top and bottom of the fabric splitting apart with no firm closure. The raw edge of the fabric is camouflaged with a stretchable lace sewn on top. After a few washings this lace falls away from the garment and leaves the raw edge of the fabric exposed. The length of the pant leg is either at the knee or just below the knee causing it to ride up or bind behind the knee. The patient will have pain walking or doing other movements like that while wearing street clothes over the garment.

The E-Z-ON garments can have market produced hooks and rounded eyes sewn on the inside of the fabric closure of the garment at a layer below the zipper. The evenly placed hooks and eyes on the inside of the garment, more often then not, press against the sites of surgical punctures in liposuction procedure and otherwise cause impingement of the tissues in other procedures. The hooks and eyes are originally covered with enamel paint, which disappears after several washings leaving bare metal against the skin.

In the prior art the fabric type is nylon or nylon mesh, which allows for undetermined compression, but for some skin types reactions can be stressful. Some patients can have heat rashes, be unable to expel perspiration, have a reaction to the fiber itself or experience other skin irritation without the flow of air to the skin. There are only two choices of color and no choice of garment style. This can be a psychological impairment to healing since some procedure can leave the patient with some depressed mood. The appearance of such a large body bandage is all important to the patient's visual image of his/her self at this critical time.

When comparing previously produced garments which function for compression of body parts pre and post surgery, the present invention provides innovative and distinct advantages over those products. The present invention uses a flexible fabric fastener which stretches, a feature not exhibited by Velcro® fasteners. The present invention has multi-sizing with it's structure and strips laid near each other will cause garments to have two or more sizes depending on the need. The flexible fabric fastener is thin, washable, dryable and adjustable. It will take on the shape of the movement of the person when sewn into a garment whilst the fabric stretches. A garment having the flexible fabric fastener, as it's principle closure, creates the opportunity for the frontal closure. Health care workers, emergency triage personnel, and the patient will have an easier time applying the garment pre and post surgery. The present invention is made of fabric that will have consistent compression for the purpose needed. It will be constructed in a durable manner thus making it possible to launder and dry the garment often. It will be suitable for rehabilitation exercises whether in or out of the water. It will have a set of three privacy cradles with each unit for cleanliness. It is cost efficient since it is one piece construction. Two garments that are uni-gender take the place of four or five garments. Multi-sizing within the garment decreases the need for more than one piece. The present invention has support panels that are woven or sewn in for security of the healing tissues and benefit of the patient psyche. The fabric will be absorbable of perspiration. Market produced hooks and eyes will be sewn to the garment for security only on the outside of the garment, thereby reducing pressure sores and or other impingements to the skin. Colors and styling of the units will be reminiscent of fashionable underwear or sports gear rather than corsets and braziers. In all ways detailed care will be taken in the manufacture of these items to prevent injury to the patient by the garment. The present invention in it's production will look for the comfort and the care of the sensitive patient and support their need for self worth.

SUMMARY OF THE INVENTION

The deficiencies of the prior art are addressed by the present invention which is directed to a compression garment employing a flexible fabric fastener. The flexible fabric fastener uses a variation of the standard hook/loop Velcro® fastening device. The flexible fabric fastener is attached to the pre/post operative garment in such a manner to allow the patient to easily move in the garment as well as to apply and remove the garment independently of healthcare workers. Two parallel elastic strips of material with Velcro®-type hooks are provided on one portion of the garment. A single elastic strip of Velcro®-type loop material would be provided on a second portion of the garment cooperating with either the first or second strips of Velcro®-type hook material to act as a fastener. Obviously, the two parallel strips of material could just as easily be the Velcro®-type loop material and the single strip of material on the cooperating second portion of the garment could be Velcro®-type hook material. As the patient heals and post operative swelling is reduced or bleeding is held internally, the three strips of cooperating Velcro®-type material acting as a flexible fabric fastener would allow a single garment to be used instead of two or more compression garments. Multi sizing the compression garment allows for pre-operative triage at an accident.

The flexible fabric fastener includes a strip of flexible, stretchable material composed of a percentage of polyester material and a percentage of rubber material. The Velcro®-type hook and loop material would be woven into a portion or portions of the surface of the flexible, stretchable backing material in an alternating pattern with an elastic locking thread pattern.

BRIEF DESCRIPTION OF THE DRAWINGS

Other objects, features and advantages of the invention will be readily apparent from the following description of certain preferred embodiments taken in conjunction with the accompanying drawings, wherein like reference characters indicate like or corresponding parts, although variations and modifications may be effected without departing from the spirit and scope of the novel concepts of the disclosure and in which.

DETAILED DESCRIPTION OF THE PREFERRED EMBODIMENTS

Figure 1:
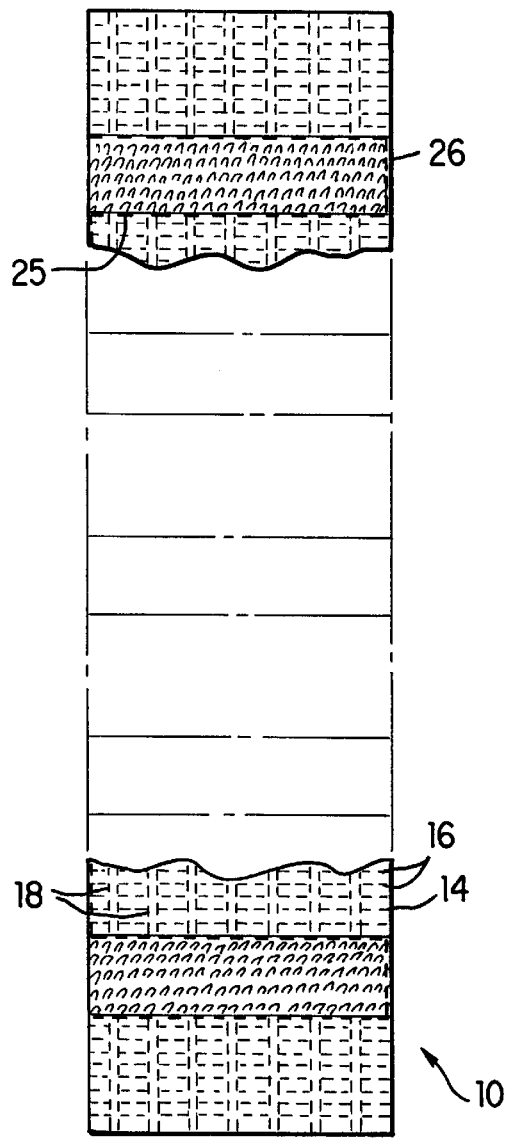
FIG. 1 is a plan view of one strip of the flexible fabric material including Velcro®-type hook elements.
Figure 1A:
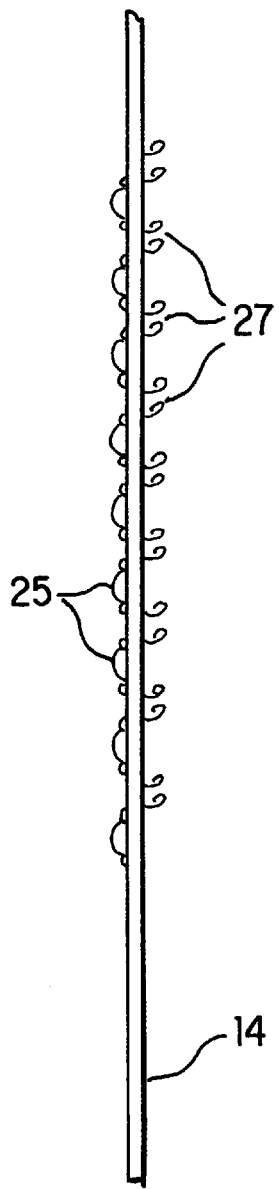
FIG. 1A is a side view showing the manner in which the Velcro®-type hook elements of FIG. 1 are woven into the elastic strip base.

FIG. 1 illustrates one strip 10 of the flexible fabric fastener. The strip 10 includes a polyester rubber elastic strip 14 provided with a plurality of horizontal threads 16 as well as a plurality of vertical threads 18. The strip 10 shows a magnified version of the flexible fabric fastener showing the threads 16 and 18 in a manner to better illustrate the present invention. In practice, the polyester rubber elastic strip 14 would include a mesh having a much larger number of horizontal threads 16 and vertical threads 18. The strip 10 shows a plurality of Velcro®-type sections of hook material 26. This Velcro®-type hook material is directly woven into the elastic material 14. FIG. 1A better illustrates the manner in which the Velcro®-like hook material 26 is attached to the polyester elastic strip 14. This pattern of alternate hook material 26 consisting of hooks 27 is woven into the elastic strip 14 by the utilization of a computerized program of weaving along with a polyester and rubber locking threads 25 woven through the elastic strip 14. This particular structure would securely and with great stability hold the hook material into place on the elastic strip 14. This structure would allow the ability of the closure to embody multiple-sizing along with soft stretchable comfort. Alternatively, the Velcro®-type hook material 26 can be woven into the entire surface of the elastic strip 14 in an alternative pattern for unlimited length of the elastic base.

Figure 2:
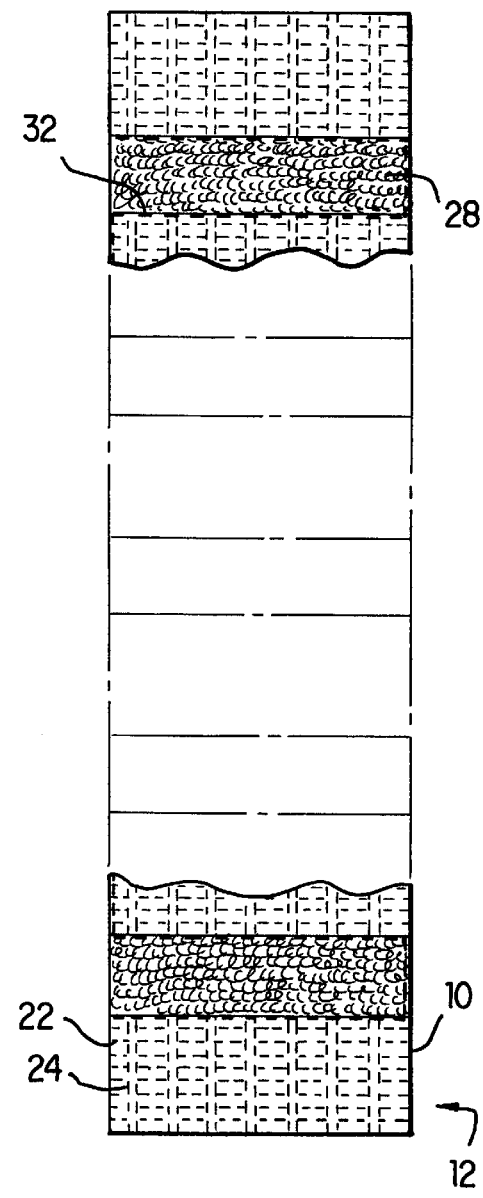
FIG. 2 is a plan view of a second strip of the flexible fabric fastener showing Velcro®-type loop material.
Figure 2A:
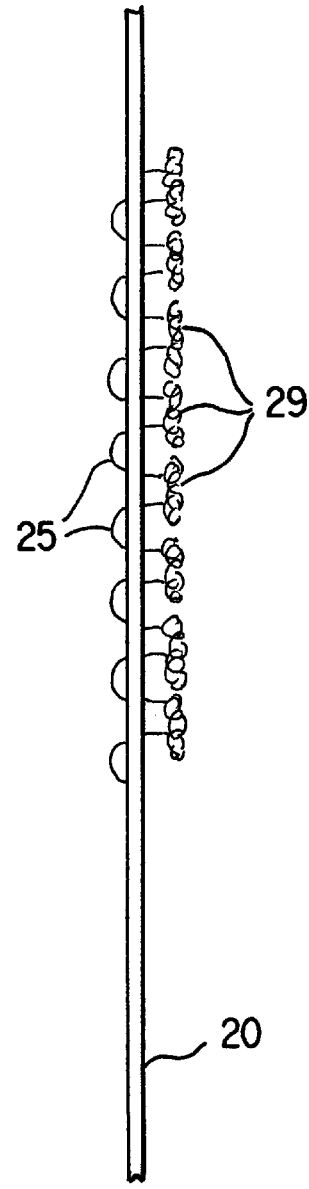
FIG. 2A is a side view of the Velcro®-type loop material of FIG. 2 woven into the elastic strip base.

FIG. 2 illustrates a second opposing strip 16 of the fastener including a stretchable elastic strip base 20 having a plurality of horizontal threads 22 as well as a plurality of vertical threads 24. In this instance, various sections of Velcro®-type loop material 28 are directly woven onto the elastic strip material 20 in a manner similar to the strip shown in FIGS. 1 and 1A. More particularly, FIG. 2A illustrates a side view of FIG. 2 including a plurality of loops 29 woven into the strip 20 using the same type of polyester and rubber locking thread 25 shown with respect to FIGS. 1 and 1A. Similar to the strip shown in FIG. 1, the entire surface of the strip 12 can have the loop material woven within the base strip 20 in a similar alternative pattern. In this manner, a number of sections of loop material 28 would cover the strip 20. However, similar to the strip shown in FIG. 1, the entire surface of the strip 20 can have the loop material woven therein.

Elastic strips 14 and 20 as well as the threads 25 and 32 are constructed from a material consisting of 75% polyester and 25% rubber. The Velcro®-type loop segment is held in place by the polyester and rubber locking thread 32 in a stable and secure pattern. However, it is noted that this exact combination of materials is not crucial to the present invention as long as these strips exhibit elasticity when they are attached stretched along the closing slits of the garment to better fit the patient. Additionally, these strips of material 14 and 20 would return to their original shape when they are no longer stretched. This feature is of great importance since this elastic fastener would be used with a number of types of garments allowing the patient to yield a comfortable pre or post-operative fit of the garment or other applications not specifically medical.

The Velcro®-type hook material and the Velcro®-type loop material shown in FIGS. 1, 1A, 2, 2A are woven into the respective strips using a computer programmed weaving pattern using an elastic type locking thread.

Figure 3:
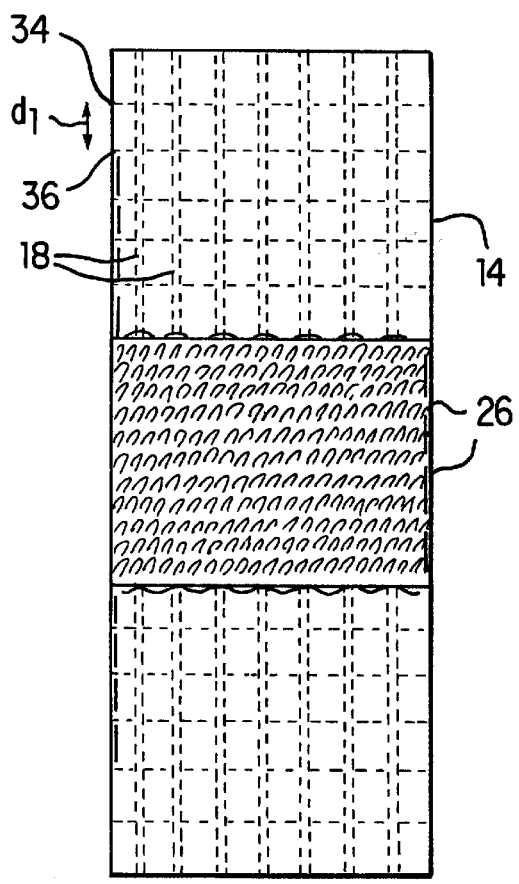
FIG. 3 is a magnified portion of the strip material of FIG. 1 in the relaxed state.
Figure 4:
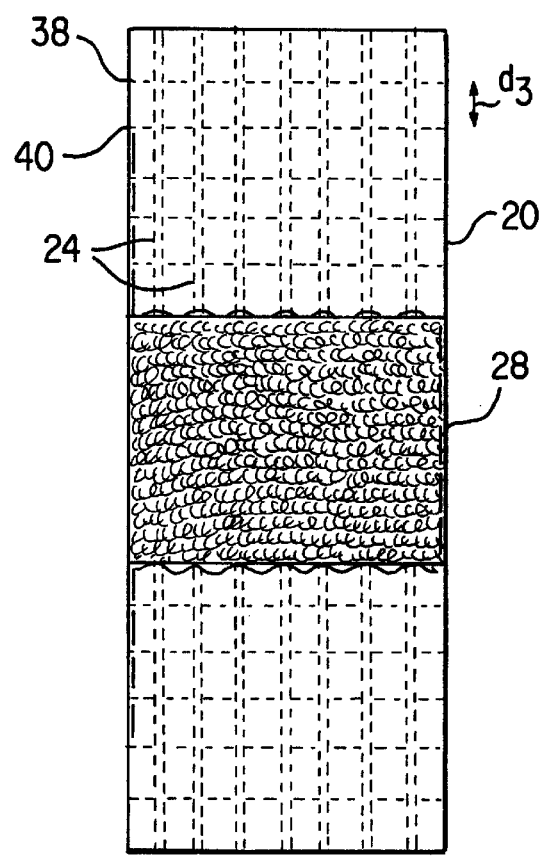
FIG. 4 is a magnified view of the strip material shown in FIG. 2 in the relaxed state.
Figure 5:
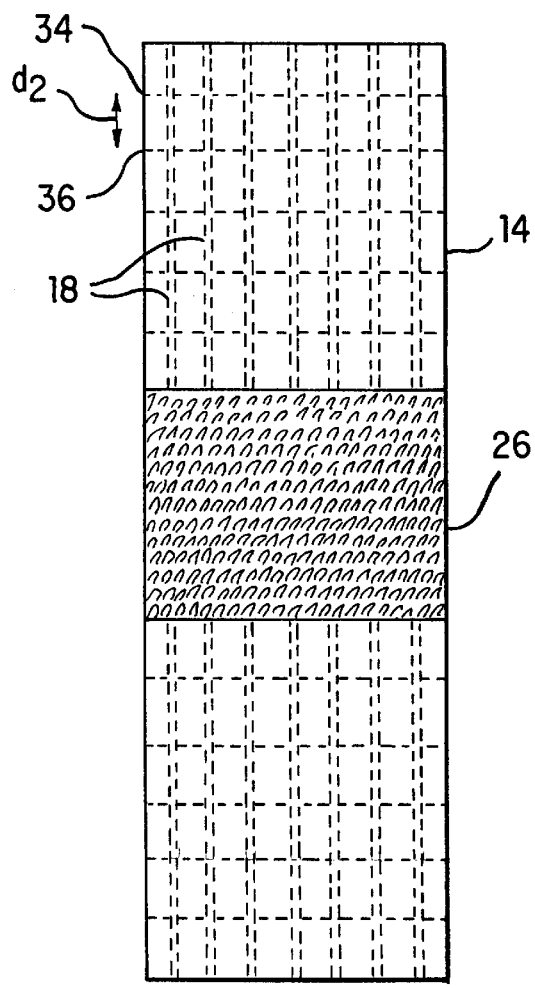
FIG. 5 is a magnified portion of the strip material shown in FIG. 1 in the stretched state.
Figure 6:
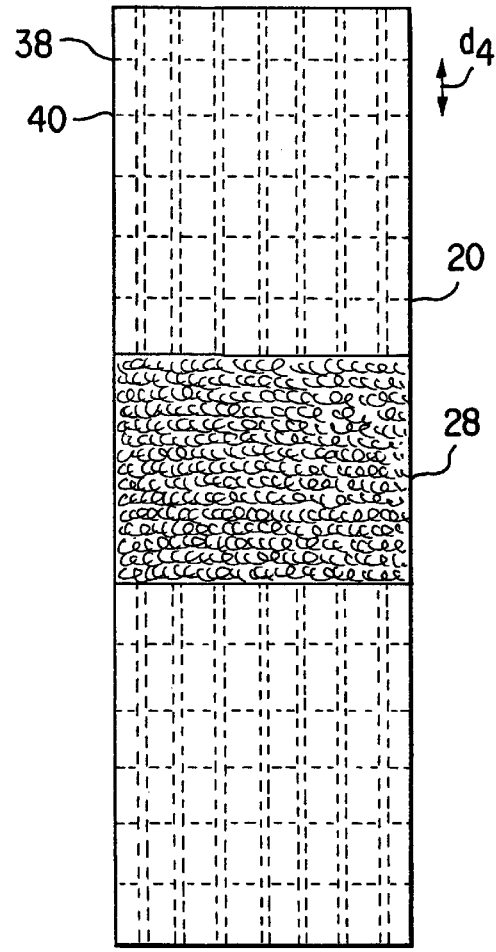
FIG. 6 is a magnified view of the strip material shown in FIG. 2 in the stretched state.

FIGS. 3 and 4 illustrate the elastic strips 14 and 20 in a more magnified view when these strips are in the relaxed state. FIGS. 5 and 6 show the same view when the strips 14 and 20 are under tension and being stretched. When the strip 14 is being stretched, the distance $d_1$ between horizontal threads 34 and 36 would be less than the distance $d_2$ between these threads 34 and 36 when the strip 14 is stretched as illustrated with respect to FIG. 5. Similarly, the distance $d_3$ between horizontal threads 38 and 40 in FIG. 4 would be less than the distance $d_4$ between these same horizontal threads 38 and 40 when the strip 20 is stretched. It is this stretchable nature that allows the flexible fabric fastener to allow it to be utilized in the various pre/post operative compression garments employed by patients who are convalescing with a pre or post-surgical swelling or bleeding.

Figure 7:
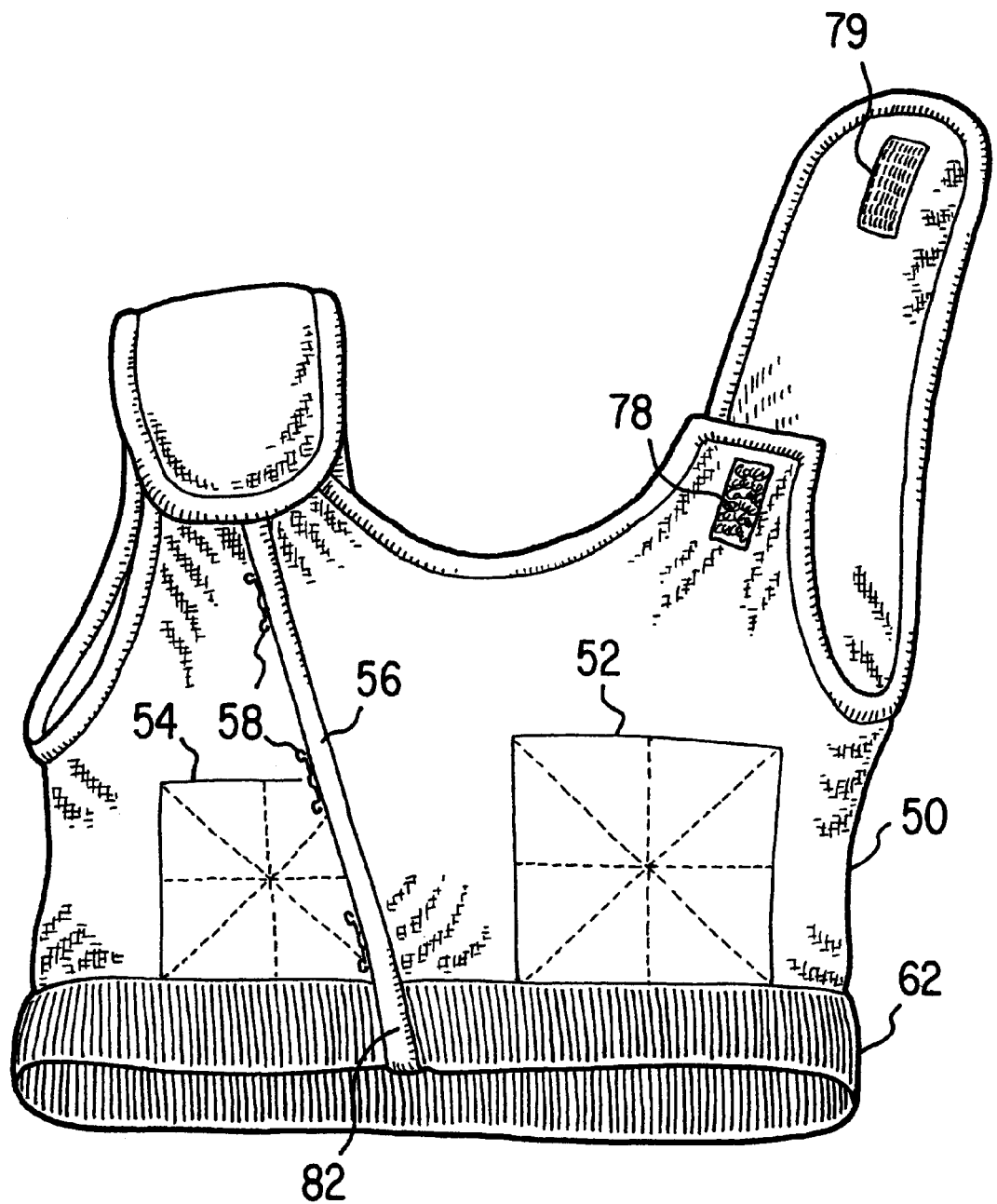
FIG. 7 is a perspective view of a post operative garment according to the present invention.
Figure 8:
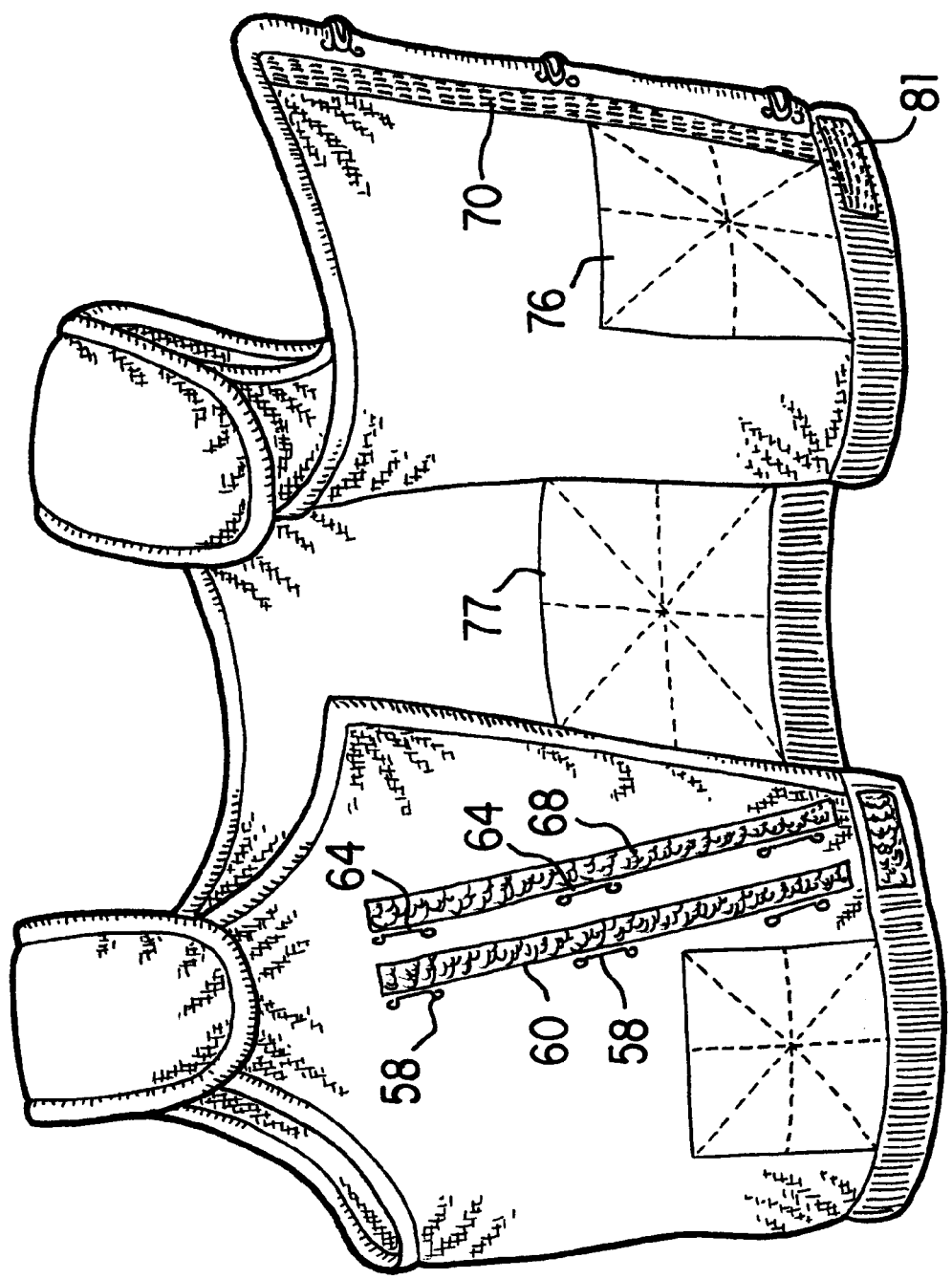
FIG. 8 is a perspective view of the garment shown in FIG. 7 in the open position.

FIGS. 7 and 8 illustrate the flexible fabric fastener of the present invention embodied in a compressible garment used by both men and women. This garment 50 is provided with sections 52 and 54 which are attached to one another utilizing the flexible fabric fastener. A cotton cloth type stretchable band cuff 62 is provided on the bottom of section 52 and 54. Appropriate arm holes 60 are used to allow the patient to wear this garment above their midriff or can be produced to reach the waist. Mechanical hook portions 58 are directly affixed to the top portion 54 and are also used as added security to the flexible fabric fasteners using eye portions 72 as shown in FIG. 8. Although not shown in FIG. 7, one strip of fastener material is provided underneath the strip section 56. As shown in FIG. 8, the portion 54 of the garment 50 is provided with two substantially parallel strips of Velcro®-type hook material 60, 68. Each of these strips 60 and 68 is sewn onto the top surface of fabric portion 54 utilizing elasticized thread. Additionally, hooks 58 and 64 are attached to the portion 54 for use with the eyes 72 provided on top section 52 to bind the two sections 52 and 54 together thereby securing the Velcro®-type loops provided on strip 70 included on the reverse side of section 52.

Similar to the strips 60, 68, the Velcro®-type loop section 70 is sewn into the material on the reverse side of section 52 with elasticized thread. Reference numeral 76 represents one of many comfort support panels inserted woven or sewn into the reverse side of section 52 (as shown) and into other positions on the reverse side of sections 52 and 54. Although strips 60, 68 and 70 illustrate the flexible fabric fastener having its own respective outside surfaces completely covered with either Velcro®-type hook or Velcro®-type loop material, it is noted that these strips can contain a plurality of distinct Velcro®-type hook or Velcro®-type loop sections as shown with respect to FIGS. 1 and 2. As illustrated with respect to FIGS. 7 and 8, when the garment 50 is initially applied to the patient, the Velcro®-type loop section 70 would cooperate with Velcro®-type loop section 68 to secure the garment in place. As the patient's physical size or swelling changes, the strip 70 would then cooperate with strip 60 to secure the garment in place for resizing. It is noted that the inclusion of the hooks 72 and the eyes 58 and 64 are optional, since the present invention could operate without their inclusion. It is noted that the exact type of eye 58, 64 is not crucial to the present invention.

Commercially produced hooks and straight eyes sewn on the edge of the outside frontal opening could be employed. This hardware would be evenly spaced, only as a security benefit to the closure. They are used on the outside of the garment to prevent painful puncture of the skin in various surgical procedures or pressure at the site of surgical entry points in liposuction. Another row of straight eyes is sewn on the outside of the garment to the second side of the garment. Only one set of hooks are needed.

Similarly, flexible fabric fasteners in the form of a Velcro®-type loop section 78 would cooperate with a Velcro®-type hook section 79 as illustrated in FIG. 7. These fasteners can be used to multi-size and stretch for comfort for the shoulder closure on both front sides of the garment. Furthermore, Velcro®-type loop sections 80 as well as Velcro®-type hook sections 81 on the lower portion of the garments shown in FIG. 8 would be used to secure cotton stretch cuffs 62 at the base of the garment together. No hooks and eyes are needed in this situation. Similarly, hooks and eyes are also not needed at the shoulder closure. The angled or slanted opening 82 allows for a secure ease of opening and closing of the garment. It is noted that this design is universal to both genders of patients.

Figure 9:
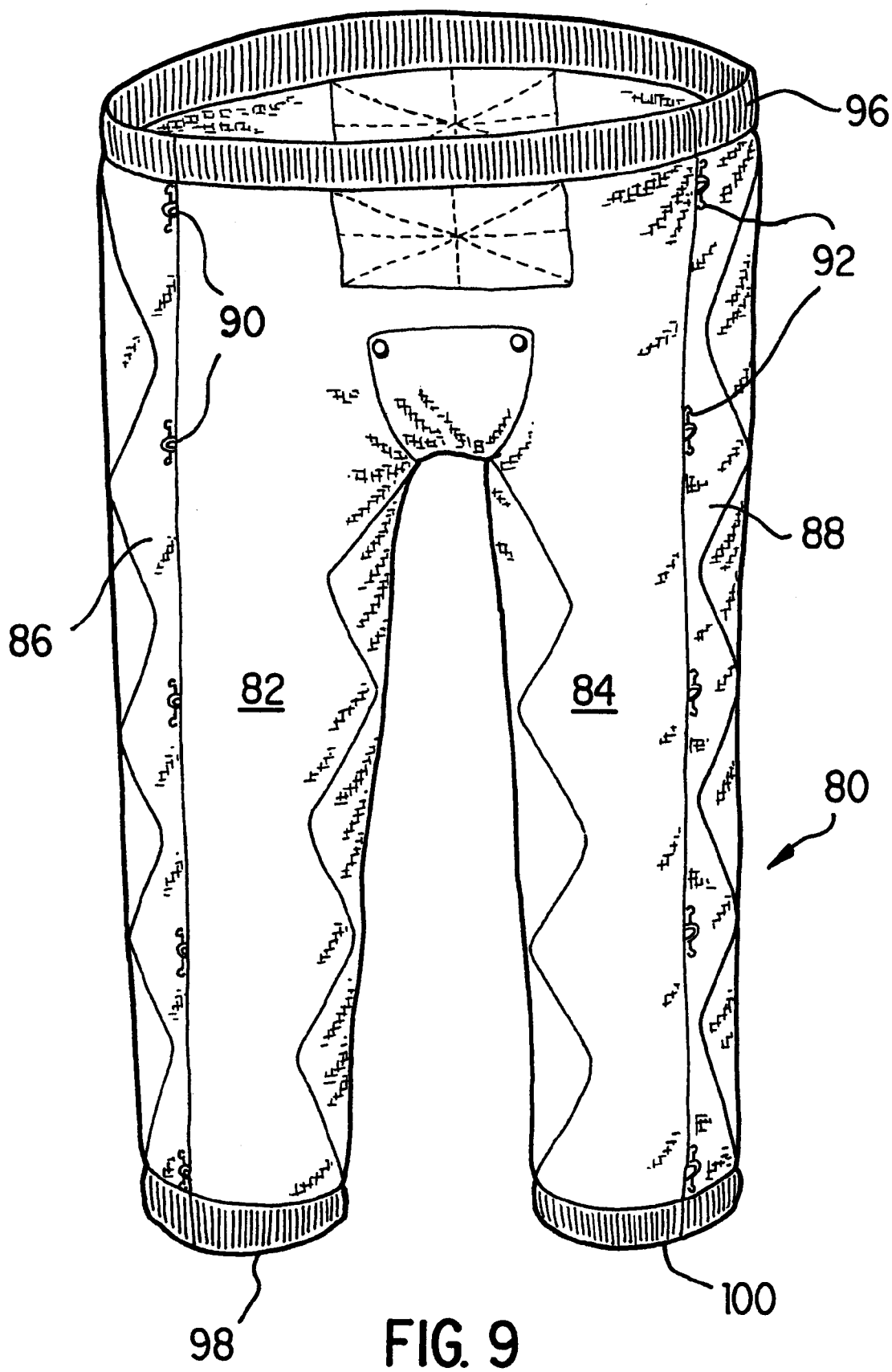
FIG. 9 is a perspective view of the post operative garment utilizing the fastener of the present invention.

FIG. 9 illustrates a compression garment 80 which can be utilized by both genders. This garment as well as the garment illustrated in FIGS. 7 and 8 is created from a cotton and Lycra® stretch material designed to allow body fluids to evaporate. The garment 80 is provided with two leg portions 82 and 84 which are affixed to the back of leg portions 86 and 88 respectively. The flexible fabric fastener according to the present invention would secure the leg portions 82 to 86 as well as leg portions 84 to 88. Hooks 90 and 92 are applied along the length of the legs from the waist to the cuff of the garment to assist in securing portion 82 to portion 86 as well as portion 88 to 84. These hooks would be used with cooperative eye portions provided on opposing parts 86, 88 of the garment. A thin elastic waistband 96 surrounds the outer portion of the garment that does not bind the body when bent or moving. Cotton cloth stretchable cuffs 98 and 100 surround the base of each part of each pant leg. A crotch portion 94 provided with snaps is included. Similar to the embodiment illustrated in FIGS. 7 and 8, the hooks and eyes are not a requirement.

Figure 10:
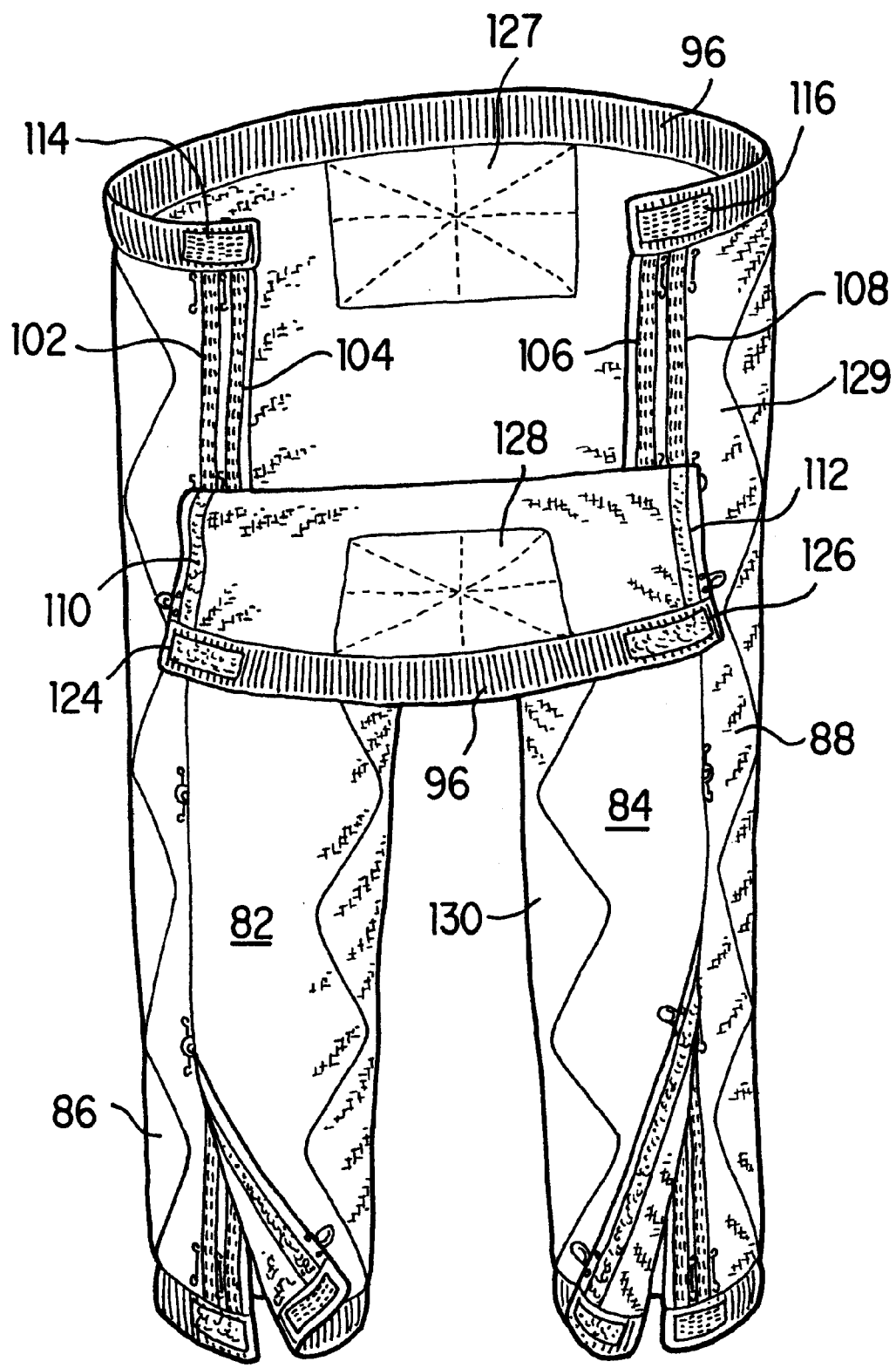
FIG. 10 is the garment shown in FIG. 9 in an opened position.

FIG. 10 illustrates the present invention with portions of the flexible fabric fasteners open to view at the center. Leg portions 86 provided with two substantially parallel elastic Velcro®-type hook fasteners 102, 104 are similar in nature to the elastic fasteners shown in FIG. 1. Similarly, the center leg portion 88 is provided with two substantially parallel elastic Velcro®-type hook fastener members 106, 108. All four of the elastic Velcro®-type hook fasteners 102, 104, 106 and 108 run continuously from the top waist portion 96 of the garment to the bottom cuff sections 98, 100 of the garment as shown in FIG. 9.

The garment shown in FIG. 9 can be accompanied by three detachable cradle pieces. At the beginning of the healing process, there is an immediate need to eliminate liquid waste without stress and strain. The crotch opening in the garment allows for this bodily function without removal of the garment. The cradle attachment is equipped with commonly available snaps. The cradle could hold sanitary or incontinence protectors. The cradle will be snapped by two snaps in the back of the garment. The cradle is drawn through the legs and snapped by two additional snaps in the front of the crotch.

While two types of compression garments have been described, it can be appreciated that a number of types of these garments can be utilized with the flexible fabric fasteners as described herein. These garments are designed to be as comfortable to the patient as possible and would be manufactured in a number of colors and designs to provide a pleasing appearance.

Once the surgical procedure is completed and a particular pre or post-surgical garment is chosen, such as the garment illustrated in FIGS. 7 and 8, a health practitioner would place the front flap portion 52 over the rear flap portion 54 attaching the Velcro®-type loop strip 70 to either of the Velcro®-type hook strips 60 or 68. The midriff waistband of the chest garment is affixed by pressing the elastic Velcro®-type loop strip 80 and elastic Velcro®-type hook strip 81 portions together. The shoulder portions are attached in the same manner. Although not necessary, the hooks and eyes as shown in FIG. 8 can also be joined together for added security. The flexible fabric fastener has two strips for comfortable sizing for the patient and will accommodate any medically applied bandages or pads placed directly on the body and hold them securely in place. When healthcare professionals are needed to inspect dressings or an incision, the market produced hooks are opened and the flexible fabric fastener can be gently drawn apart by one person. Additionally, the frontal opening is convenient.

The lower body garment as shown in FIGS. 9 and 10 are applied in the same manner except for the loose front flaps. These flaps are brought together from the flattened back piece through the legs. One side leg portion is attached to its adjacent portion and the other side leg portion is attached to its adjacent leg portion at the center front of leg. The waist portions are secured to one another as are the bottom cuff portions with sizeable flexible fabric fasteners. Similar to the top portion, the bottom portion has two sizes built in due to the double strip of the elastic Velcro®-type strip hook and loop combinations. Sizing can be done at the point of the surgical procedure or triage and to accommodate surgically placed pads or other medical coverings or devices.

While the present invention has been described particularly with use on upper or lower torsos, other compression garments can incorporate the flexible fabric fasteners. Other garments can be used to cover specific portions of the body, such as a single arm or leg or the head. The flexible fabric fastener can provide multi-sizing in any or all compression type garments or any mundane stretchable fabric garment.

Furthermore, it is believed that many additional modifications can be made which would be in the purview of one possessing ordinary skill in the art.

What is claimed is:

1. A pre or post surgical compression garment comprising:
    a stretchable chest encircling garment having a first end and a second end, said first end and said second end removably attached to each other to produce a compression garment;

an attachment device for securing said first end to said second end, said attached device including
  a first strip of flexible elastic mesh material having a top surface, said first strip sewn to the underside of the top surface of said first end;
  Velcro®-type hook material installed through to at least a portion of the top surface of said first strip;
  a second strip of flexible elastic mesh material having a top surface, said second strip of material sewn to the top surface of said second end; and
  Velcro®-type loop material installed through to at least a portion of the top surface of said second strip;
wherein when tension is applied to either the first end of the garment or the second end of the garment, at least one of said strips of flexible material would stretch to more easily accommodate the wearer of the garment when said first strip of material is removably attached to said second strip of material, thereby securing the first end of the garment to the second end of the garment.

2. The pre or post surgical compression garments in accordance with claim 1, wherein said first and second strips of flexible elastic mesh material is a composite material of polyester and rubber.

3. The pre or post surgical compression garments in accordance with claim 2, wherein said composite material is stretch lycra and cotton.

4. The pre or post-operative compression garment in accordance with claim 1, further including a third strip of flexible elastic mesh material having a top surface, said third strip applied to the first end of the garment substantially parallel to said second strip of flexible elastic mesh material and further comprising Velcro®-type loop material installed through to at least a portion of the top surface of said third strip, wherein said first strip of mesh material is removably attached to either said second strip of elastic mesh material or said third strip of mesh material to secure the first end of the garment to the second end of the garment.

5. The post-operative compression garment in accordance with claim 1, including a third strip of flexible elastic mesh material having a top surface, said third strip applied to the second end of the garment substantially parallel to said second strip of flexible elastic mesh material and further comprising Velcro®-type loop material installed through to at least a portion of the top surface of said second and third strip, wherein said first strip of elastic flexible mesh material is removably attached to either said second strip of elastic flexible mesh material or said third strip of elastic flexible mesh material to secure the first end of the garment to the second end of the garment.

6. The pre or post-operative compression garment in accordance with claim 1 wherein said Velcro®-type hook material is woven through or installed into the top surface of said first strip as a plurality of transverse strips and said Velcro®-type loop material is woven through or installed into the top surface of said second and third strip as a plurality of transverse strips.

7. The pre or post-operative compression garments in accordance with claim 1 wherein said Velcro®-type hook material is attached to said first strip of flexible elastic mesh by a composite polyester and rubber locking thread, and said Velcro®-type loop material is attached to said second and third strips of flexible elastic mesh material by a composite polyester and rubber locking thread.

8. The pre or post-operative compression garment in accordance with claim 1, further including leg portions attached to said garment.

9. A pre or post operative compression garment comprising:
  a stretchable first fabric component covering the lower back of a patient and a portion of both legs, said first fabric component having a top surface provided with a first end and a second end;
  a first strip of flexible elastic mesh material having a top surface, said first strip sewn to said underside of a top surface of said first end of said first fabric component;
  a second strip of flexible elastic mesh material having a top surface, said second strip sewn to said underside of a top surface of said second end of said second fabric component;
  Velcro®-type hook material installed through to at least a portion of said top surface of said first strip of flexible elastic mesh material and said second strip of flexible elastic mesh material;
  a stretchable first and second fabric component covering the front of a patient and a portion of both legs, said second fabric component provided with a first end and a second end and a bottom surface;
  a first strip of flexible elastic mesh material having a top surface, said first strip sewn to said top of the bottom surface of said first end and said second fabric component;
  a second strip of flexible mesh material having a top surface, said second strip sewn to said top of the bottom surface of said second end of said second fabric component; and
  has Velcro®-type loop material installed through at least a portion of said top surface of said first strip of flexible elastic mesh material and said second strip of flexible elastic mesh material;
wherein when tension is applied to either said first or second fabric component, at least one of said strips of flexible elastic mesh material would stretch to more easily accommodate the patient when said first strip of flexible elastic mesh is removably attached to said first strip of flexible elastic mesh material and said second strip of flexible elastic mesh material is removably attached to said second strip of flexible elastic mesh material, thereby securing said first fabric portion to said second fabric portion.

10. The pre or post-surgical compression garment in accordance with claim 9, wherein said first, second and third flexible fabric fastener on each side of the fabric component is a composite material of polyester and rubber with nylon hooks or loops.

11. The pre or post-surgical compression garment in accordance with claim 10, wherein said composite material is lycra and cotton.

12. The pre or post-operative garment in accordance with claim 1, wherein said Velcro®-type hook material is woven or installed through at least a portion of the top surface of said first strip and said Velcro®-type loop material is woven or installed through at least a portion of the top surface of said first strip.

13. The pre or post-operative compression garment in accordance with claim 12, wherein said Velcro®-type hook material is installed or woven into said first strip and said Velcro®-type loop material is installed or woven into said second strip using an elastic locking thread.

14. The pre or post-operative compression garment in accordance with claim 8, further including stretchable cotton cuffs attached to said leg portion and midriff portion with the flexible fabric fastener connecting together the two sides of the midriff cuff and the two sides of the leg cuffs.

15. The pre or post-operative compression garment in accordance with claim 8, further including one or more support panels applied to said stretchable chest encircling garment, the pre or post-operational compression garment for the lower body garment further including at least three support panels continuously placed from the waist to the lower cotton cuff on the outer hip and thigh area, as well as at least three support panels continuously sewn or woven in from crotch to lower cotton cuff creating seamless connections for front and back portions of the garment, said support panels woven or sewn into the lower back of said chest encircling garment as well as at the front and back waist of the lower body garment.

16. The pre or post-operative compression garment in accordance with claim 8, further including a cradle at the crotch in said garment.

17. The pre or post operative compression garment in accordance with claim 9, further comprising at least three support panels attached to said stretchable first fabric component provided continuously from the top of said first fabric component to the bottom of said first fabric component and further comprising at least three support panels continuously sewn or woven from a crotch portion to a cotton portion creating seamless connections for the front and back portions of said garment.

* * * * *